United States Patent
Hyun et al.

(10) Patent No.: US 9,283,148 B2
(45) Date of Patent: Mar. 15, 2016

(54) MULTI-PURPOSE SYRINGE

(75) Inventors: Dongchul D. Hyun, Brea, CA (US); Michael T. Fleury, Brea, CA (US)

(73) Assignee: MEDELA HOLDING AG, Baar (CH)

( * ) Notice: Subject to any disclaimer, the term of this patent is extended or adjusted under 35 U.S.C. 154(b) by 341 days.

(21) Appl. No.: 13/041,850

(22) Filed: Mar. 7, 2011

(65) Prior Publication Data

US 2012/0232524 A1    Sep. 13, 2012

(51) Int. Cl.

| | |
|---|---|
| *A61M 31/00* | (2006.01) |
| *A61M 5/178* | (2006.01) |
| *A61M 5/31* | (2006.01) |
| *A61J 9/00* | (2006.01) |
| *A61J 15/00* | (2006.01) |
| *A61J 11/00* | (2006.01) |
| *A61J 1/10* | (2006.01) |
| *A61J 7/00* | (2006.01) |

(52) U.S. Cl.
CPC ................ *A61J 7/0053* (2013.01); *A61J 15/00* (2013.01); *A61J 15/0003* (2013.01); *A61M 5/178* (2013.01); *A61J 1/10* (2013.01); *A61J 9/00* (2013.01); *A61J 11/0005* (2013.01); *A61J 15/0011* (2013.01); *A61M 31/00* (2013.01); *A61M 2005/3117* (2013.01)

(58) Field of Classification Search
CPC ..... A61J 9/00; A61J 15/0011; A61J 11/0005; A61J 15/0003; A61J 15/00; A61J 1/10; A61J 7/0053; A61M 31/00; A61M 5/178; A61M 2005/3117
USPC ........................... 604/181, 514, 192–198, 110
See application file for complete search history.

(56) References Cited

U.S. PATENT DOCUMENTS

| | | | |
|---|---|---|---|
| 5,032,117 A * | 7/1991 | Motta | 604/88 |
| 5,344,407 A * | 9/1994 | Ryan | 604/192 |
| 5,616,135 A * | 4/1997 | Thorne et al. | 604/192 |
| RE39,107 E * | 5/2006 | Shaw | 604/110 |
| D654,585 S | 2/2012 | Costello et al. | |
| 8,357,117 B2 * | 1/2013 | Sokal et al. | 604/76 |
| 8,992,488 B2 | 3/2015 | Ingram et al. | |
| 9,028,438 B2 | 5/2015 | Ingram et al. | |
| 2007/0060898 A1 * | 3/2007 | Shaughnessy | A61M 39/10 604/284 |
| 2007/0167914 A1 * | 7/2007 | Leong et al. | 604/168.01 |
| 2014/0207098 A1 | 7/2014 | Ingram et al. | |
| 2015/0148753 A1 | 5/2015 | Ingram et al. | |

OTHER PUBLICATIONS www.marianmedicalonline.com; "SuperLock—Oral/Enteral Safety Syringes", 1 pg, May 13, 2011.
www.marianmedicalonline.com; Medicine Enteral Syringe Pump, 1 pg, May 13, 2011.

(Continued)

*Primary Examiner* — Emily Schmidt
*Assistant Examiner* — Lauren M Peng
(74) *Attorney, Agent, or Firm* — Stetina Brunda Garred & Brucker

(57) ABSTRACT

A multi-purpose syringe that may be used both for gravity feeding and syringe pump assisted feeding of a neonate is disclosed. The multi-purpose syringe includes a cap and a plunger. The cap and plunger may be selectively engaged to the barrel depending on whether the neonate is fed by gravity or syringe pump. The cap seals the top of the barrel but allows gas to pass between the inside of the barrel and the environment and traps liquid within the barrel. To this end, the cap has an aperture covered by a hydrophobic member.

11 Claims, 4 Drawing Sheets

(56) References Cited

OTHER PUBLICATIONS

New Era Pump Systems, Inc.; "Precise Programmable Syringe Pumps", 2 pgs, May 13, 2011.
Enteral Syringe with Non-Circular Cross-Section, U.S. Appl. No. 61/382,720, filed Sep. 14, 2010, pp. 1-20.
Coating Composition for Use with Photoresist Compositions, U.S. Appl. No. 61/428,963, filed Dec. 31, 2010, pp. 1-21.
Enteral Feeding and Reflux Collection System and Method Using Vented Syringe, U.S. Appl. No. 61/549,308, filed Oct. 20, 2011, pp. 1-11.

* cited by examiner

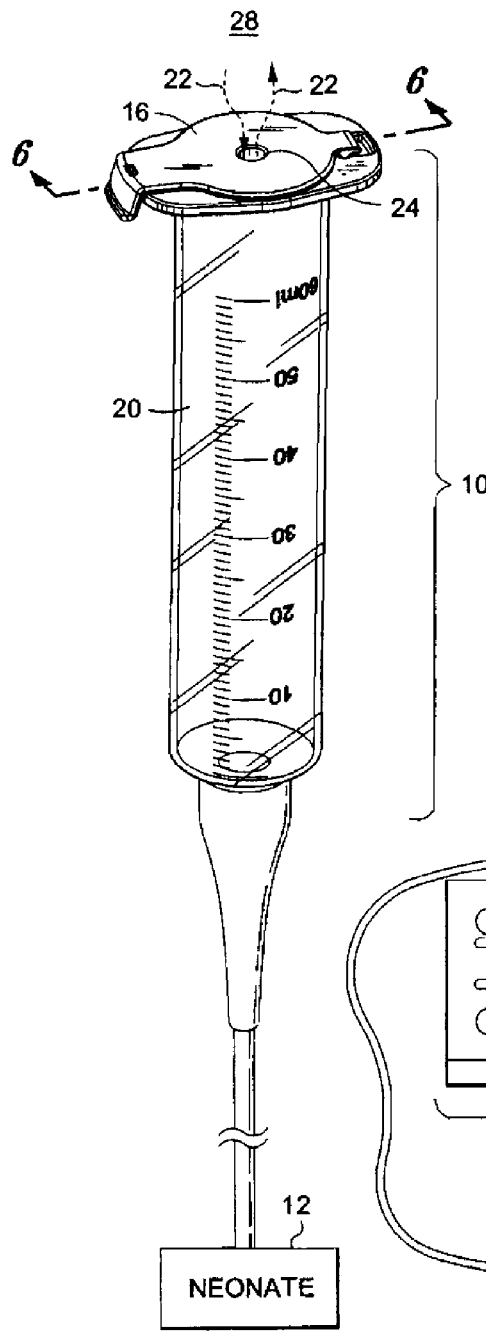
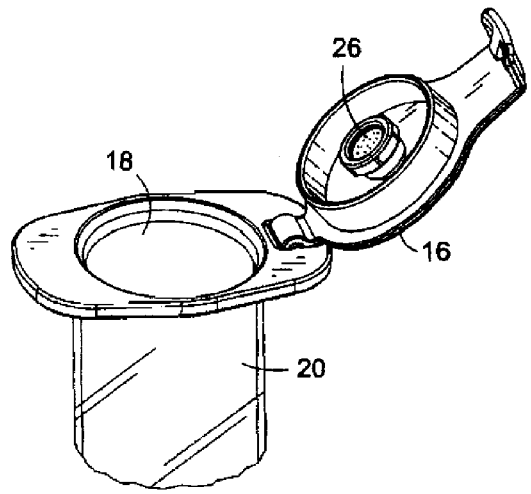
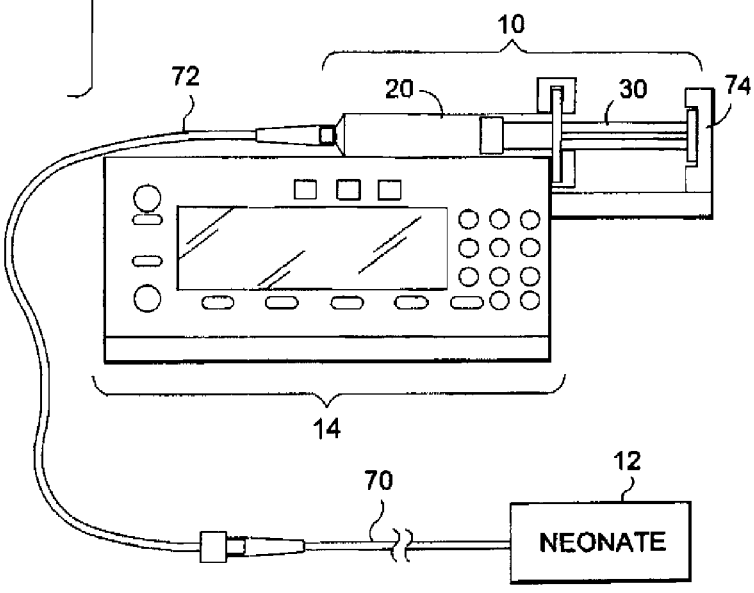
Fig. 1
Fig. 3
Fig. 2

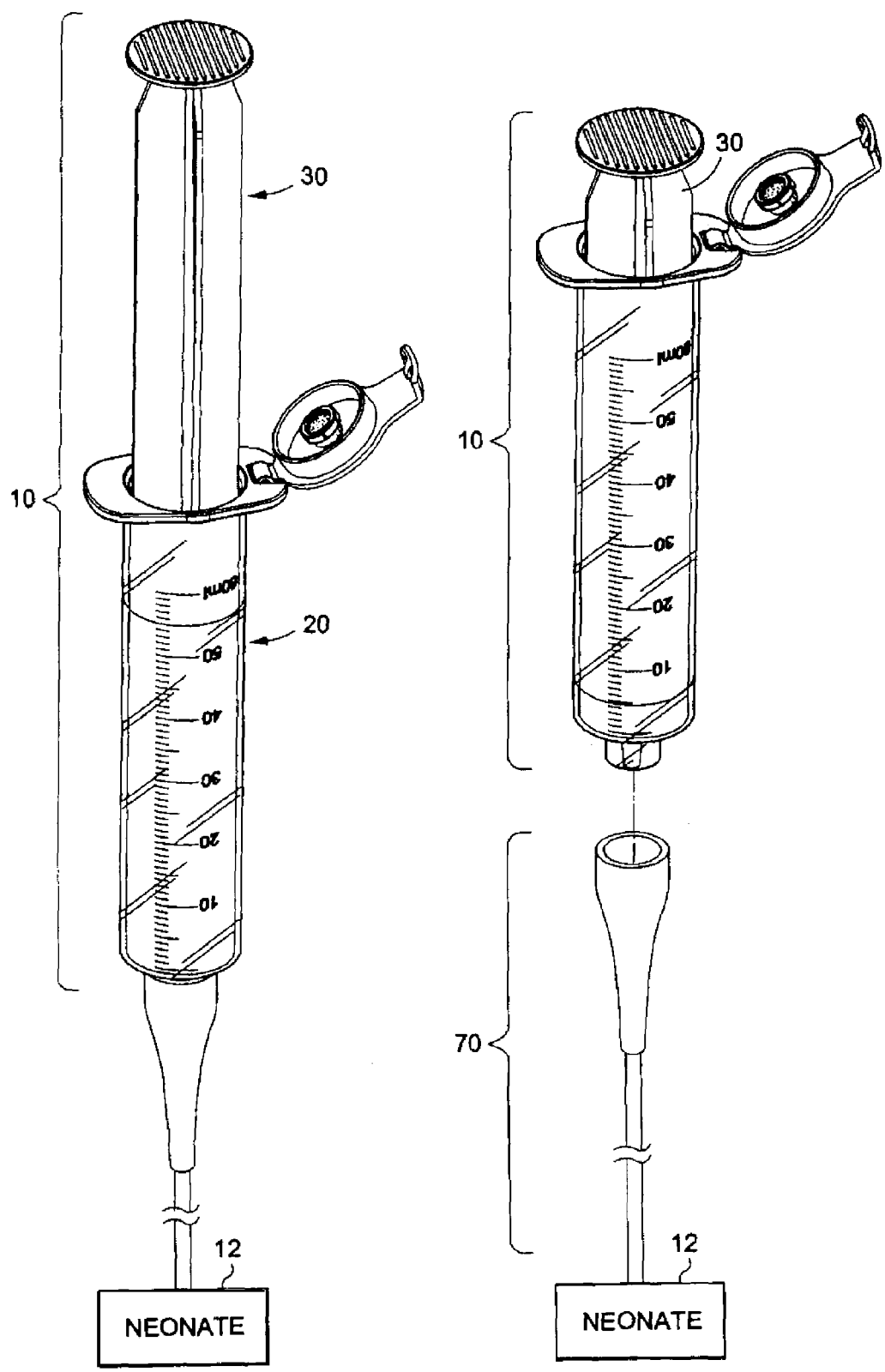

MULTI-PURPOSE SYRINGE

CROSS-REFERENCE TO RELATED APPLICATIONS

Not Applicable

STATEMENT RE: FEDERALLY SPONSORED RESEARCH/DEVELOPMENT

Not Applicable

BACKGROUND

The embodiments disclosed herein relate to a syringe for feeding a neonate.

There are generally two methods for feeding a neonate. The first method utilizes a syringe pump which meters out enteral fluid such as breast milk and/or neonate formula to the neonate. The second method is a gravity feed method wherein the syringe is filled with enteral fluid and held above the neonate to allow gravity to draw the enteral fluid to the neonate.

In both methods, a feeding tube is inserted through the neonate's mouth or nose and into the neonate's stomach. The syringe is connected to the feeding tube. A plunger of the syringe is retracted to check for residual fluid in the neonate's stomach. After residual fluid is checked, residual fluid is pushed back into the stomach of the neonate. Enteral fluid such as breast milk and/or neonate formula is then poured into the syringe. If the neonate is fed with the assistance of a syringe pump, a plunger is inserted into the back end of the syringe and the syringe is mounted to the syringe pump. The syringe pump is programmed with the amount of fluid and feeding time then started. After the neonate is fed, the plunger is removed from the feeding syringe to prepare the syringe for venting. A small gauze pad is disposed in the back end of a barrel of the syringe. The barrel is then connected to the feeding tube to begin the venting process wherein gas within the neonate's stomach is allowed to escape, but reflux fluid is retained within the barrel of the feeding syringe. The gauze pad retains the reflux fluid in the syringe, but does so ineffectively. In this example, the syringe must always be held above the level of the neonate, since placing the feeding syringe below the level of the neonate would cause the reflux fluid to spill out of the barrel. Additionally, even if the syringe is held above the neonate, the gauze pad is a clumsy method of retaining reflux fluid in the syringe. As such, reflux fluid may still spill out of the syringe and cause a mess.

For gravity feeding, the barrel with the enteral fluid filled therein is held above the neonate. Unfortunately, the barrel is exposed to the environment and susceptible to contamination from airborne particulate. Moreover, during the venting process, the same problem with spillage of reflux fluid arises as described above in relation to the syringe pump assisted feeding process described above.

Accordingly, there is a need in the art for an improved feeding syringe.

BRIEF SUMMARY

The feeding syringe described herein addresses the needs discussed above, discussed below and those that are known in the art.

The feeding syringe may have a cap that is removably attachable to a barrel of the syringe. The cap forms a seal that allows gas to pass through an aperture formed in the cap, but does not allow liquid to pass through the aperture due to a hydrophobic member that covers the aperture. The feeding syringe may be used for both gravity feeding and syringe pump assisted feeding. In gravity feeding, a plunger of the syringe is removed from a barrel. The cap is engaged to the top of the barrel. With enteral fluid disposed within the barrel and the cap engaged to the barrel, a feeding syringe is held above the neonate while the enteral fluid is gravity fed into the neonate's stomach through a feeding tube. The cap prevents contamination of the enteral fluid. For syringe pump assisted feeding, the cap is removed or displaced out of the way. A plunger is disposed in the barrel. With enteral fluid disposed in the barrel of the syringe, the syringe is then mounted to the syringe pump which pushes the plunger into the barrel at a predefined rate to flow enteral fluid into the neonate by way of the feeding tube. Also, during a venting process for both gravity and pump feeding, no gauze pad is needed. The cap has a hydrophobic filter to prevent reflux enteral fluid from spilling out of the barrel but allows gas to pass through the aperture during the venting process. Additionally, the syringe does not necessarily have to be elevated above the neonate during the venting process. The multi-purpose feeding syringe may perform all three processes, namely, check for residual enteral fluid, feeding and venting. The multi-purpose feeding syringe may also be used in the gravity feed method or syringe pump assisted method. Accordingly, the multi-purpose syringe reduces the chance of contaminating the enteral fluid and reduces inventory needs for hospitals which reduces costs.

More particularly, a multi-purpose syringe capable of feeding a neonate by gravity or with assistance of a syringe pump is disclosed. The syringe may comprise a barrel, a plunger, finger tabs, a cap and a hydrophobic filter. The barrel may define an output and an entrance. The plunger may slide within the barrel for forcing enteral fluid out of the output into the neonate. The plunger may be removably disposable in the barrel. Finger tabs may be disposed adjacent to the entrance of the barrel for assisting a user in depressing the plunger into the barrel. One of the finger tabs may have a hinge. The cap is removably attachable to the hinge and the entrance of the barrel. When the cap is attached to the entrance of the barrel, the cap may be pivoted between a closed position wherein the cap seals the entrance of the barrel and an opened position wherein the cap is displaced away from the entrance of the barrel. The cap may have an aperture for allowing gas to communicate between the barrel and an environment. The hydrophobic filter element may be disposed over the aperture of the cap for allowing gas to pass therethrough and provide a liquid barrier between the barrel and the environment.

The plunger may be removed from the barrel and the cap attached to the hinge. The cap may be pivoted to the closed position during gravity feeding. An outer periphery of the cap may be sealed to an inner periphery of the entrance of the barrel to seal the entrance of the barrel when the cap is disposed in the closed position. Alternatively, the plunger may be disposed within the barrel and the cap either pivoted to the opened position or removed from the hinge during feeding with assistance of the syringe pump.

The hinge may be a round cross member integrated into at least one of the finger tabs. The cap may have a clip with a cylindrical cavity that is engageable to the round cross member for pivoting the cap between the closed and opened positions. The round cross member may define a central axis along a length of the round cross member. The central axis of the round cross member may be transverse to a central axis of the barrel wherein the central axis of the barrel is along a length of the barrel. The cylindrical cavity of the clip may have an open end for removably attaching the clip to the round cross member. The cap may have a latch removably engagable to the barrel of the syringe for locking the cap in the closed position. A lip of the latch is removably engageable to an edge of one of the finger tabs.

Alternatively, the finger tab may incorporate a clip with a cylindrical cavity integrated into at least one of the finger tabs. The cap may have a round cross member that is engageable to the cylindrical cavity of the clip for pivoting the cap between the closed and opened positions. In this instance, the cylindrical cavity of the clip may define a central axis along a length of the cylindrical cavity. The central axis of the cylindrical cavity may be transverse to a central axis of the barrel wherein the central axis of the barrel is along a length of the barrel. The cylindrical cavity of the clip has an open end for removably attaching the clip to the round cross member.

Additionally, a method for feeding a neonate with a multi-purpose syringe capable of feeding a neonate by gravity or syringe pump is disclosed. The method may comprise the steps of inserting an enteral feeding tube into a neonate; pulling on a plunger of the syringe to check for residual liquid within the stomach of the neonate; pushing back the residual liquid into the stomach of the neonate; filling the syringe with enteral liquid; engaging the syringe to a syringe pump; feeding the neonate; after feeding, disposing a cap onto an entrance of the syringe to seal the entrance of the syringe; allowing gas to flow through a hydrophobic filter integrated into the cap and trapping reflux liquid within the barrel.

The disposing the cap step may include the step of engaging a clip of the cap to a round cross member incorporated in a finger tab of the barrel.

Moreover, a method for feeding a neonate with a multi-purpose syringe capable of feeding a neonate by gravity or syringe pump is disclosed. The method may comprise the steps of inserting an enteral feeding tube into a neonate; pulling on a plunger of the syringe to check for residual liquid within the stomach of the neonate; pushing back the residual liquid into the stomach of the neonate; removing a plunger from a barrel of the syringe; filling the syringe with enteral liquid; disposing a cap onto an entrance of the syringe to seal the entrance of the syringe; after disposing the cap step, feeding the neonate; after the feeding step, allowing gas to flow through a hydrophobic filter integrated into the cap and trapping reflux liquid within the barrel.

The feeding step may include the step of disposing the filled syringe above the neonate to allow gravity to flow enteral fluid into the neonate.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 1 is a perspective view of a syringe;

FIG. 2 is a schematic view of a syringe for feeding a neonate with the assistance of a syringe pump;

FIG. 3 is an enlarged view of a first embodiment of a cap in an open position with respect to the barrel shown in FIG. 1;

FIG. 5 is a perspective view of a syringe with a plunger inserted therein with the plunger in a retracted position;

FIG. 7 is a perspective view of the syringe and plunger shown in FIG. 5 with the plunger in a depressed state.

DETAILED DESCRIPTION

Figure 4:
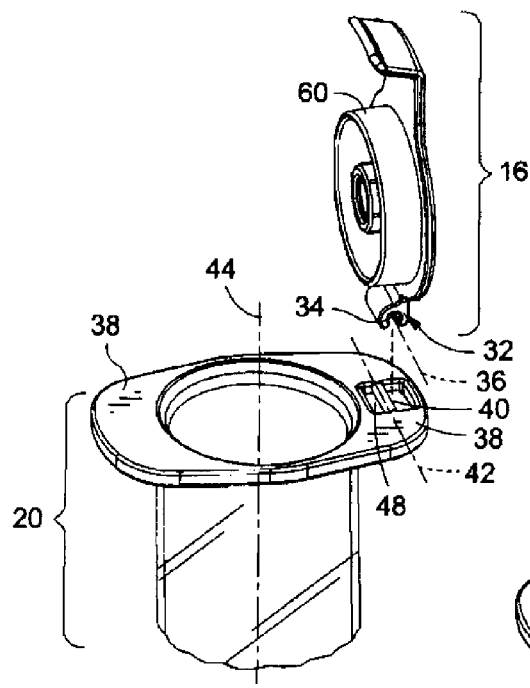
FIG. 4 is a perspective view of the cap detached from the barrel shown in FIG. 3.

Referring now to the drawings, the multi-purpose syringe may be used to feed a neonate 12 by way of gravity as shown in FIG. 1 or with the assistance of a syringe pump 14 as shown in FIG. 2. The multi-purpose syringe 10 includes a cap 16 that may seal off an entrance 18 (see FIG. 3) of a barrel 20 of the multi-purpose syringe 10. When the cap 16 seals off the entrance 18 of the barrel 20, gas 22 (see FIG. 1) is allowed to pass through an aperture 24 formed in the cap 16. The aperture 24 is covered with a hydrophobic member 26 (see FIG. 3) to provide a liquid barrier between the interior of the barrel 20 and an environment 28 yet allow gas to pass therethrough. During gravity feeding, enteral fluid (e.g. breast milk or neonate formula) is poured into the barrel 20 and fed to the neonate by way of gravity. Air is introduced into the barrel 20 through aperture 24 to permit gravity feeding during the gravity feeding process. For syringe pump 14 assisted feeding, the cap 16 may be removed from the barrel 20 as shown in FIG. 4. Enteral fluid is poured into the barrel 20 and a plunger 30 is inserted into the barrel 20 as shown in FIG. 5. The syringe 10 is mounted to the syringe pump 14 shown in FIG. 2 which then feeds the neonate 12. After feeding, the syringe 10 may be removed from the syringe pump 14 and the cap 16 may be placed back on the barrel 20 to seal off the entrance 18, as shown in FIG. 1. At this point, for both the gravity feeding process and the syringe pump assisted feeding process, venting is allowed to remove gas from the neonate. Gas passes through the hydrophobic filter 26 but traps reflux fluid in the barrel 20. Although the syringe 10 is preferably held above the neonate, it is not necessary.

Accordingly, the multi-purpose syringe 10 may be used for both gravity feeding as well as syringe pump 14 assisted feeding. Moreover, the syringe 10 may be used to check for residual fluid, feeding, and for venting after feeding without creating a mess from spilled reflux enteral fluid since the cap 16 and hydrophobic filter 26 trap the liquid/reflux fluid in the barrel 20, but allow gas to pass through the hydrophobic filter 26 and aperture 24. Additionally, the syringe does not need to be elevated above the neonate since the cap 16 and hydrophobic filter 26 are effective at trapping the liquid in the barrel and allowing gas to pass therethrough during the venting process. Moreover, as will be further discussed below, the multi-purpose syringe may be used to check for residual fluid, perform feeding and venting. Since one syringe does all three processes, there is a reduced opportunity for contaminating the enteral liquid and infecting the neonate. Lastly, the multi-purpose syringe reduces inventory requirements and reduces cost since one syringe 10 may be used for multiple purposes.

Figure 6:
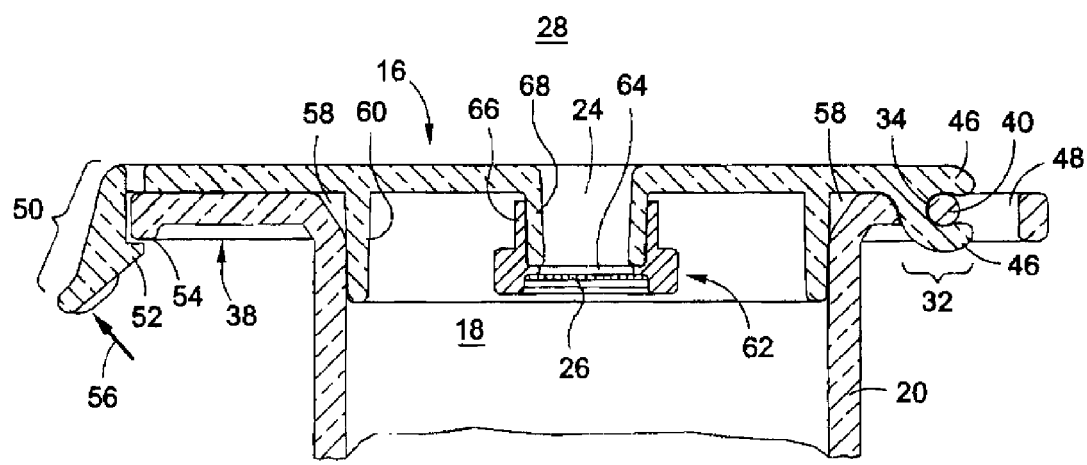
FIG. 6 is a cross-sectional view of the cap and barrel shown in FIG. 1.

More particularly, the cap 16 is removably attachable to the barrel 20 as shown in FIGS. 3 and 4. The cap incorporates a clip 32 that has a cylindrical cavity 34. The cylindrical cavity 34 defines a central axis 36 that extends lengthwise through the cylindrical cavity 34. The barrel 20 has finger tabs 38. The finger tabs 38 are used to assist in depressing the plunger 30 further into the barrel 20 when needed. One of the finger tabs 38 may incorporate a round cross member 40 which defines a hinge. The round cross member 40 also has a central axis 42 that extends along a length of the round cross member 40. The round cross member 40 is positioned on the finger tab 38 so that its central axis 42 is perpendicular to a central axis 44 of the barrel 20. The central axis 44 extends along the length of the barrel 20. The round cross member 40 is positioned so that its central axis 42 does not intersect the central axis 44 of the barrel 20. The round cross member 40 is sized and configured to fit within the cylindrical cavity 34 as shown in FIG. 6. The clip 32 preferably circumscribes the round cross member 40 more than 180° so that tangs 46 of the clip 32 must spread open in order to insert or remove the round cross member 40 in or out of the cylindrical cavity 34. Once the clip 32 is attached to the round cross member 40, pressure is required to remove the cap 16 from the barrel 20 and cannot be removed by gravity alone. To form the round cross member 40, one of the finger tabs 38 may have an aperture 48 (see FIGS. 4 and 6). The round cross member 40 may extend across the aperture 48 and be positioned as described above.

Figure 4A:
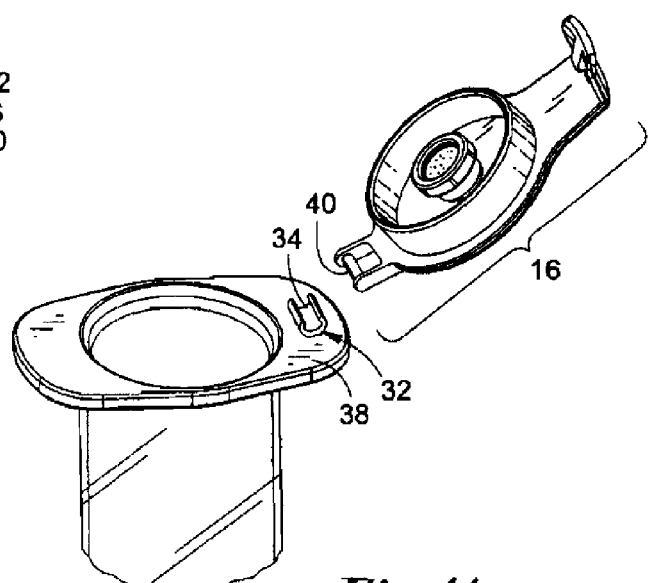
FIG. 4A is a second embodiment of an attachment mechanism for removably attaching the cap and the barrel.
Figure 4B:
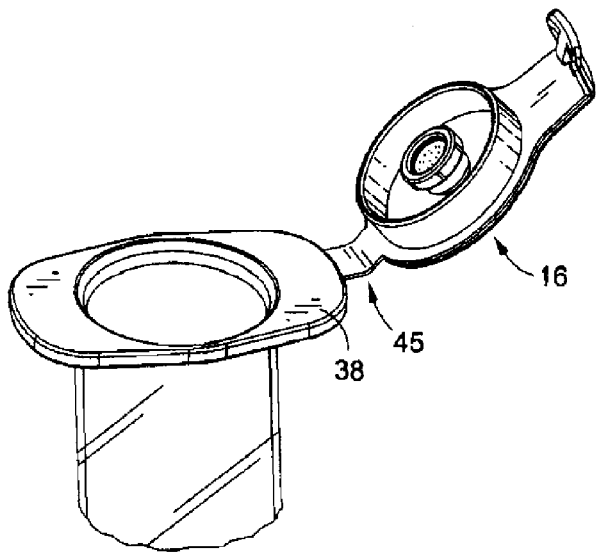
FIG. 4B is a third embodiment of the cap and barrel having a living hinge.

Other ways of removably attaching the cap 16 to the barrel 20 are also contemplated. By way of example and not limitation, the round cross member 40 may be formed on the cap 16 and the clip 32 may be formed on one of the finger tabs 38, as shown in FIG. 4A. Additionally, it is contemplated that the cap 16 may be permanently attached to the finger tab 38 by way of a living hinge 45, as shown in FIG. 4B.

The cap 16 may be pivoted about the round cross member 40 to the closed position (see FIG. 6) and locked in that position. To this end, the cap 16 may have a latch 50 which engages the other one of the finger tabs 38. In particular, the latch 50 has a lip 52 that engages an edge 54 of the finger tab 38. The latch 50 is flexible so that the lip 52 is biased against the edge 54 when the cap 16 is in the closed position. To remove or pivot the cap 16 to the open position (see FIG. 3), the user lifts the latch 50 in the direction of arrow 56 to bend the latch 50 and cap 16 and displace the lip 52 away from the edge 54. Once the lip 52 is clear from the edge 54, the user may pivot or rotate the cap 16 about the round cross member 40 to the opened position. Once the cap 16 is in the opened position, the user may move the cap 16 out of the way (see FIG. 3) or remove the cap 16 from the barrel 20, as shown in FIG. 4, with the application of force to remove the round cross member 40 from the cylindrical cavity 34 of the clip 32.

Referring now to FIG. 6, the hydrophobic filter 26 covers the aperture 24 so that gas but not liquid passes between the inside of the barrel 20 and the environment 28. The cap 16 also prevents spillage of fluid (e.g. gas and liquid) from the outer perimeter 58 of the entrance 18 of the barrel 20. The cap 16 has a cylindrical flange 60 which is shown in FIGS. 4 and 6. The cylindrical flange 60 is pressed against an inner surface of the barrel 20. In particular, an outer diameter of the cylindrical flange 60 may be equal to or slightly greater than the inner diameter of the barrel 20. As the cap 16 is being disposed in the closed position, the entire circumference of the cylindrical flange 60 contacts and provides an air and fluid tight seal with the inner surface of the barrel 20. Accordingly, no fluid such as gas or liquid is allowed to escape out of the barrel 20 from the outer perimeter 58 of the entrance 18. The hydrophobic filter 26 is secured to a mount 62. The mount 62 may have an aperture 64 which is covered by the hydrophobic member 26. The mount 62 additionally has a flange 66 which is connected to a flange 68 of the cap 16. The flange 66 may be sealed and secured to the flange 68 by way of adhesive, mechanical fastening or sonic welding.

In use, the syringe is used to feed a neonate by gravity or with the assistance of a syringe pump 14. To utilize the multi-purpose syringe 10 with the syringe pump 14, a feeding tube 70 (see FIG. 2) is inserted into the stomach of the neonate 12. The syringe 10 is connected to the feeding tube 70 with the plunger 30 in the depressed position as shown in FIG. 7. With the syringe 10 connected to the feeding tube 70, the plunger 30 is retracted to check for residual enteral liquid in the neonate's stomach 12. After checking for residual enteral fluid, the residual enteral fluid is pushed back into the stomach of the neonate 12. To feed the neonate with a syringe pump 14, the syringe 10 is removed from the feeding tube 70. An extension tube 72 (see FIG. 2) is connected to the feeding tube 70. The syringe 10 is filled with enteral fluid. The plunger 30 is disposed within the barrel 20 of the syringe 10. The cap 16 may be moved out of the way (see FIG. 3) or removed from the barrel 20 (see FIG. 4). The syringe 10 is connected to the extension tube 72 and mounted to the syringe pump 14 as shown in FIG. 2. The syringe pump 14 is programmed to traverse the plunger 30 of the syringe 10 at a certain rate depending on the neonate 12. During feeding, a lever 74 (see FIG. 2) of the syringe pump 14 pushes the plunger 30 into the barrel 20 at a certain predefined rate until the prescribed amount of enteral fluid is dispensed and fed into the neonate 12. After the neonate 12 is fed, the operator may remove the plunger 30 from the barrel 20 and place the cap 16 back on the barrel 20. The cap 16 is then traversed to the closed position (see FIG. 6). At this point, the venting process may begin. Preferably, the syringe 10 is held above the elevation of the neonate 12. The syringe 10 may be elevated above the neonate 12 to prevent reflux fluid from escaping out of the syringe 10. However, elevating the syringe 10 above the neonate is not necessary. The cap 16 is sealed against the entrance of the barrel 20. The cap 16 has an aperture covered with a hydrophobic filter which allows the passage of gas but not liquid therethrough. The reflux fluid is trapped within the syringe 10 even if the syringe 10 is held below the level of the neonate 12 during venting.

To feed the neonate 12 by gravity with the multi-purpose syringe 10, residual enteral fluid is checked and pushed back into the neonate 12 as discussed above. The plunger 30 is removed from the barrel 20. Also, enteral fluid is filled into the barrel of the syringe. The cap 16 is placed over the entrance 18 of the barrel 20 to seal off the barrel 20, as shown in FIG. 1. The syringe 10 is raised above the level of the neonate to allow gravity to draw enteral fluid in the barrel 20 into the stomach of the neonate 12. Air is allowed to pass through the aperture 24 of the cap 16 and through the hydrophobic member 26. Other contaminants are prevented from entering the interior of the barrel 20 because the cap 16 seals off and prevents entrance of any contaminants into the barrel 20. The syringe 10 may be hung on a stand so that the syringe 10 is located about 8 to 10 inches above the neonate 12 during gravity feeding. After the feeding process, the syringe 10 is left in place until the venting process is completed. During the venting process, gas or air is allowed to escape through the aperture 24 of the cap 16 but reflux fluid is trapped within the barrel 20 since liquid such as reflux fluid is not allowed to pass through the aperture 24 of the cap 16 due to the hydrophobic member 26. Preferably, the syringe 10 is held above the elevation of the neonate 12 but may be laid below the elevation of the neonate 12 since reflux fluid will be trapped within the barrel 20 by the cap 16 but gas allowed to pass through the hydrophobic member 26.

The above description is given by way of example, and not limitation. Given the above disclosure, one skilled in the art could devise variations that are within the scope and spirit of the invention disclosed herein, including various ways of fabricating the barrel. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A multi-purpose neonate feeding syringe for feeding a neonate by gravity or with assistance of a syringe pump having a syringe barrel mounting member and a syringe plunger traversal member, the syringe comprising:
   a syringe plunger cooperatively engageable to the syringe plunger traversal member;
   a barrel defining an output and an entrance, the barrel being sufficiently rigid so that the plunger is slidable within the barrel and capable of forcing enteral fluid out of the output into the neonate when the plunger is traversed in a direction from the entrance to the output of the barrel, the barrel fixedly engagable to the syringe barrel mounting member so that the plunger is pushed into the barrel as the syringe plunger traversal member is traversed toward the syringe barrel, the plunger being removably disposable in the barrel;
   finger tabs disposed adjacent to the entrance of the barrel for assisting a user in depressing the plunger into the barrel;
   a cap attached to the barrel with a hinge and displaceable away from the entrance of the barrel, the cap being pivotable between a closed position wherein the cap seals the entrance of the barrel and an opened position wherein the cap is displaced away from the entrance of the barrel, the cap having an aperture for allowing gas to communicate between the barrel and an environment;
   a hydrophobic filter element disposed over the aperture of the cap for allowing gas to pass therethrough and providing a liquid barrier between the barrel and the environment;
   wherein the plunger is removed from the barrel and the cap is pivoted about the hinge to the closed position for gravity feeding and the plunger is disposed within the barrel and the cap is displaced away from the entrance of the barrel for syringe pump assisted feeding so that the barrel may be used either for gravity feeding or syringe pump assisted feeding.

2. The syringe of claim 1 wherein an outer periphery of the cap is sealed to an inner periphery of the entrance of the barrel to seal the entrance of the barrel when the cap is disposed in the closed position.

3. The syringe of claim 1 wherein the hinge is a round cross member integrated into at least one of the finger tabs, and the cap has a clip with a cylindrical cavity that is engagable to the round cross member for pivoting the cap between the closed and opened positions.

4. The syringe of claim 3 wherein the round cross member defines a central axis along a length of the round cross member, the central axis of the round cross member being transverse to a central axis of the barrel wherein the central axis of the barrel is along a length of the barrel.

5. The syringe of claim 3 wherein the cylindrical cavity of the clip has an open end for removably attaching the clip to the round cross member.

6. The syringe of claim 1 wherein the cap has a latch removably engageable to the barrel of the syringe for locking the cap in the closed position.

7. The syringe of claim 6 wherein a lip of the latch is removably engageable to an edge of one of the finger tabs.

8. The syringe of claim 1 wherein the finger tab incorporates a clip with a cylindrical cavity integrated into at least one of the finger tabs, and the cap has a round cross member that is engageable to the cylindrical cavity of the clip for pivoting the cap between the closed and opened positions.

9. The syringe of claim 8 wherein the cylindrical cavity of the clip defines a central axis along a length of the cylindrical cavity, the central axis of the cylindrical cavity being transverse to a central axis of the barrel wherein the central axis of the barrel is along a length of the barrel.

10. The syringe of claim 8 wherein the cylindrical cavity of the clip has an open end for removably attaching the clip to the round cross member.

11. The syringe of claim 1 wherein the cap is removably attachable to the entrance of the barrel.

\* \* \* \* \*